(12) United States Patent
Abrevaya et al.

(10) Patent No.: US 7,314,964 B2
(45) Date of Patent: Jan. 1, 2008

(54) CATALYTIC NAPHTHA CRACKING CATALYST AND PROCESS

(75) Inventors: Hayim Abrevaya, Des Plaines, IL (US); Suheil F. Abdo, Des Plaines, IL (US); R. Lyle Patton, Surprise, AZ (US)

(73) Assignee: UOP LLC, Des Plaines, IL (US)

( * ) Notice: Subject to any disclaimer, the term of this patent is extended or adjusted under 35 U.S.C. 154(b) by 422 days.

(21) Appl. No.: 10/990,450

(22) Filed: Nov. 17, 2004

(65) Prior Publication Data

US 2005/0075526 A1   Apr. 7, 2005

Related U.S. Application Data

(63) Continuation of application No. 10/246,801, filed on Sep. 17, 2002, now Pat. No. 6,867,341.

(51) Int. Cl.
C07C 4/06 (2006.01)
(52) U.S. Cl. .................. 585/651; 585/652; 585/653
(58) Field of Classification Search ........... 585/651, 585/652, 653
See application file for complete search history.

(56) References Cited

U.S. PATENT DOCUMENTS

| | | | |
|---|---|---|---|
| 3,928,483 A | 12/1975 | Chang et al. | 260/668 |
| 3,954,600 A | 5/1976 | Gladrow et al. | 208/119 |
| 4,025,575 A | 5/1977 | Chang et al. | 260/682 |
| 4,076,842 A | 2/1978 | Plank et al. | 423/328 |
| 4,172,812 A | 10/1979 | Winter | 208/72 |
| 4,176,049 A | 11/1979 | Winter et al. | 208/70 |
| 4,200,520 A | 4/1980 | Gladrow et al. | 208/120 |
| 4,208,269 A | 6/1980 | Gladrow et al. | 208/120 |
| 4,239,654 A | 12/1980 | Gladrow et al. | 252/455 |
| 4,252,479 A | 2/1981 | Scherfenberg | 406/182 |
| 4,287,048 A | 9/1981 | Gladrow et al. | 208/120 |
| 4,287,166 A | 9/1981 | Dwyer et al. | 423/325 |
| 4,289,606 A | 9/1981 | Gladrow et al. | 208/120 |
| 4,308,129 A | 12/1981 | Gladrow et al. | 208/120 |
| 4,447,669 A | 5/1984 | Hamon et al. | 585/640 |
| 4,496,786 A | 1/1985 | Santilli et al. | 585/640 |
| 4,499,314 A | 2/1985 | Seddon et al. | 585/408 |
| 4,547,616 A | 10/1985 | Avidan et al. | 585/640 |
| 4,584,091 A | 4/1986 | Pine | 208/114 |
| 4,677,243 A | 6/1987 | Kaiser | 585/638 |
| 4,814,316 A | 3/1989 | Pellet et al. | 502/214 |
| 4,830,728 A | 5/1989 | Herbst et al. | 208/78 |
| 4,843,183 A | 6/1989 | Inui | 585/640 |
| 4,861,938 A | 8/1989 | Lewis et al. | 585/640 |
| 4,923,594 A | 5/1990 | Pellet et al. | 208/114 |
| 4,944,864 A | 7/1990 | Kugler | 208/120 |
| 4,973,792 A | 11/1990 | Lewis et al. | 585/638 |
| 5,026,935 A | 6/1991 | Leyshon et al. | 585/315 |
| 5,026,936 A | 6/1991 | Leyshon et al. | 585/315 |
| 5,043,522 A | 8/1991 | Leyshon et al. | 585/651 |
| 5,069,776 A | 12/1991 | Biswas et al. | 208/120 |
| 5,095,163 A | 3/1992 | Barger | 585/640 |
| 5,120,893 A | 6/1992 | Gabriel et al. | 585/653 |
| 5,126,308 A | 6/1992 | Barger et al. | 502/214 |
| 5,191,141 A | 3/1993 | Barger et al. | 585/640 |
| 5,414,181 A | 5/1995 | Bearden, Jr. et al. | 585/654 |
| 5,447,622 A | 9/1995 | Kerby et al. | 208/78 |
| 5,489,726 A | 2/1996 | Huss, Jr. et al. | 585/671 |
| 5,491,273 A | 2/1996 | Santiesteban et al. | 585/639 |
| 5,582,711 A | 12/1996 | Ellis et al. | 208/76 |
| 5,714,663 A | 2/1998 | Serrand et al. | 585/648 |
| 5,770,043 A | 6/1998 | Ellis et al. | 208/76 |
| 5,770,044 A | 6/1998 | Ellis et al. | 208/76 |
| 5,788,834 A | 8/1998 | Lapinski | 208/118 |
| 5,824,208 A | 10/1998 | Bienstock et al. | 208/76 |
| 5,846,403 A | 12/1998 | Swan et al. | 208/113 |
| 5,952,539 A | 9/1999 | Seimandi et al. | 585/648 |
| 5,958,366 A | 9/1999 | Smith et al. | 423/700 |
| 5,990,369 A | 11/1999 | Barger et al. | 585/640 |
| 6,033,555 A | 3/2000 | Chen et al. | 208/52 |
| 6,049,017 A | 4/2000 | Vora et al. | 585/324 |
| 6,069,287 A | 5/2000 | Ladwig et al. | 585/648 |
| 6,080,303 A | 6/2000 | Cao et al. | 208/120.01 |
| 6,090,271 A | 7/2000 | Carpency et al. | 208/113 |
| 6,093,867 A | 7/2000 | Ladwig et al. | 585/648 |
| 6,106,697 A | 8/2000 | Swan et al. | 208/77 |
| 6,118,035 A | 9/2000 | Fung et al. | 585/653 |
| 6,150,293 A | 11/2000 | Verduijn et al. | 502/67 |
| 6,179,993 B1 | 1/2001 | Seimandi et al. | 208/27 |
| 6,211,104 B1 | 4/2001 | Shi et al. | 502/67 |
| 6,258,257 B1 | 7/2001 | Swan, III et al. | 208/74 |
| 6,300,537 B1 | 10/2001 | Strohmaier et al. | 585/653 |
| 6,307,117 B1 | 10/2001 | Tsunoda et al. | 585/651 |
| 6,313,366 B1 | 11/2001 | Ladwig et al. | 585/648 |
| 6,339,181 B1 | 1/2002 | Chen et al. | 585/653 |
| 6,399,540 B1 | 6/2002 | Oki et al. | 502/350 |
| 6,410,813 B1 | 6/2002 | Dath et al. | 585/653 |
| 6,416,660 B1 | 7/2002 | Zanibelli et al. | 208/216 |

FOREIGN PATENT DOCUMENTS

EP    0 109 059    11/1983

(Continued)

OTHER PUBLICATIONS

Kaiser, V. and Picciotti, M.; "Better Ethylene Separation Unit" *Hydrocarbon Processing* Nov. 1988, 57-61.

(Continued)

*Primary Examiner*—Thuan Dinh Dang
(74) *Attorney, Agent, or Firm*—Frank S Mounaro; Arthur E Gooding

(57) ABSTRACT

A process is disclosed for enhancing the production of light olefins using a catalyst with small pores. The catalyst comprises a molecular sieve having 10 membered rings with channels of limited length. The molecular sieve has a high silica to alumina ratio and has pores sized to limit production of aromatics in the cracking process.

5 Claims, 9 Drawing Sheets

FOREIGN PATENT DOCUMENTS

| | | |
|---|---|---|
| EP | 0 109 060 | 11/1983 |
| EP | 0501577 | 2/1992 |
| EP | 0 951 444 | 10/1997 |
| EP | 0 911 308 | 4/1999 |
| EP | 0909582 | 4/1999 |
| EP | 0909804 | 4/1999 |
| EP | 1 157 735 | 11/2001 |
| WO | WO 96/16004 | 5/1996 |
| WO | WO 97/45197 | 12/1997 |
| WO | WO 98/56740 | 12/1998 |
| WO | WO 98/56873 | 12/1998 |
| WO | WO 99/28032 | 6/1999 |
| WO | WO 99/57226 | 11/1999 |
| WO | WO 99/61553 | 12/1999 |
| WO | WO 00/10948 | 3/2000 |
| WO | WO 00/17105 | 3/2000 |
| WO | WO 00/76648 | 6/2000 |
| WO | WO 00/40672 | 7/2000 |

OTHER PUBLICATIONS

IZA Structure Commission. "Welcome to the Database of Zeolite Structures" Slate Aug. 22, 2002. <www..iza-structure.org/databases/>, date not available.

CATALYTIC NAPHTHA CRACKING CATALYST AND PROCESS

CROSS-REFERENCE TO RELATED APPLICATION

This application is a Continuation of application Ser. No. 10/246,801 filed Sep. 17, 2002, now U.S. Pat. No. 6,867,341 the contents of which are hereby incorporated by reference in its entirety.

FIELD OF THE INVENTION

The present invention relates to a process for the production of light olefins from a naphtha feed stream. This invention also relates to an improved zeolite used in the process for producing light olefins.

BACKGROUND OF THE INVENTION

Ethylene and propylene, light olefin hydrocarbons with two or three atoms per molecule, respectively, are important chemicals for use in the production of other useful materials, such as polyethylene and polypropylene. Polyethylene and polypropylene are two of the most common plastics found in use today and have a wide variety of uses for both as a material fabrication and as a material for packaging. Other uses for ethylene and propylene include the production of vinyl chloride, ethylene oxide, ethylbenzene and alcohol. Steam cracking or pyrolysis of hydrocarbons produces essentially all of the ethylene and propylene. Hydrocarbons used as feedstock for light olefin production include natural gas, petroleum liquids, and carbonaceous materials including coal, recycled plastics or any organic material.

An ethylene plant is a very complex combination of reaction and gas recovery systems. The feedstock is charged to a cracking zone in the presence of steam at effective thermal conditions to produce a pyrolysis reactor effluent gas mixture. The pyrolysis reactor effluent gas mixture is stabilized and separated into purified components through a sequence of cryogenic and conventional fractionation steps. A typical ethylene separation section of an ethylene plant containing both cryogenic and conventional fractionation steps to recover an ethylene product with a purity exceeding 99.5% ethylene is described in an article by V. Kaiser and M. Picciotti, entitled, "Better Ethylene Separation Unit." The article appeared in HYDROCARBON PROCESSING MAGAZINE, November 1988, pages 57-61 and is hereby incorporated by reference.

Methods are known for increasing the conversion of portions of the products of the ethylene production from a zeolitic cracking process to produce more ethylene and propylene by a disproportionation or metathesis of olefins. Such processes are disclosed in U.S. Pat. No. 5,026,935 and U.S. Pat. No. 5,026,936 wherein a metathesis reaction step is employed in combination with a catalytic cracking step to produce more ethylene and propylene by the metathesis of $C_4$ and heavier molecules. The catalytic cracking step employs a zeolitic catalyst to convert a hydrocarbon stream having 4 or more carbon atoms per molecule to produce olefins having fewer carbon atoms per molecule. The hydrocarbon feedstream to the zeolitic catalyst typically contains a mixture of 40 to 95 wt-% paraffins having 4 or more carbon atoms per molecule and 5 to 60 wt-% olefins having 4 or more carbon atoms per molecule. In U.S. Pat. No. 5,043,522, it is disclosed that the preferred catalyst for such a zeolitic cracking process is an acid zeolite, examples includes several of the ZSM-type zeolites or the borosilicates. Of the ZSM-type zeolites, ZSM-5 was preferred. It was disclosed that other zeolites containing materials which could be used in the cracking process to produce ethylene and propylene included zeolite A, zeolite X, zeolite Y, zeolite ZK-5, zeolite ZK-4, synthetic mordenite, dealuminized mordenite, as well as naturally occurring zeolites including chabazite, faujasite, mordenite, and the like. Zeolites which were ion-exchanged to replace alkali metal present in the zeolite were preferred. Preferred cation exchange cations were hydrogen, ammonium, rare earth metals and mixtures thereof.

European Patent No. 109,059B1 discloses a process for the conversion of a feedstream containing olefins having 4 to 12 carbon atoms per molecule into propylene by contacting the feedstream with a ZSM-5 or a ZSM-11 zeolite having a silica to alumina atomic ratio less than or equal to 300 at a temperature from 400 to 600° C. The ZSM-5 or ZSM-11 zeolite is exchanged with a hydrogen or an ammonium cation. The reference also discloses that, although the conversion to propylene is enhanced by the recycle of any olefins with less than 4 carbon atoms per molecule, paraffins which do not react tend to build up in the recycle stream. The reference provides an additional oligomerization step wherein the olefins having 4 carbon atoms are oligomerized to facilitate the removal of paraffins such as butane and particularly isobutane which are difficult to separate from $C_4$ olefins by conventional fractionation. In a related European Patent 109060B1, a process is disclosed for the conversion of butenes to propylene. The process comprises contacting butenes with a zeolitic compound selected from the group consisting of silicalites, boralites, chromosilicates and those zeolites ZSM-5 and ZSM-11 in which the mole ratio of silica to alumina is greater than or equal to 350. The conversion is carried out at a temperature from 500 to 600° C. and at a space velocity of from 5 to 200 kg/hr of butenes per kg of pure zeolitic compound. The European Patent 109060B1 discloses the use of silicalite-1 in an ion-exchanged, impregnated, or co-precipitated form with a modifying element selected from the group consisting of chromium, magnesium, calcium, strontium and barium.

Molecular sieves such as the microporous crystalline zeolite and non-zeolitic catalysts, particularly silicoaluminophosphates (SAPO), are known to promote the conversion of oxygenates to ethylene and propylene mixtures. Numerous patents describe this process for various types of these catalysts: U.S. Pat. No. 3,928,483, U.S. Pat. No. 4,025,575, U.S. Pat. No. 4,252,479 (Chang et al.); U.S. Pat. No. 4,496,786 (Santilli et al.); U.S. Pat. No. 4,547,616 (Avidan et al.); U.S. Pat. No. 4,677,243 (Kaiser); U.S. Pat. No. 4,843,183 (Inui); U.S. Pat. No. 4,499,314 (Seddon et al.); U.S. Pat. No. 4,447,669 (Harmon et al.); U.S. Pat. No. 5,095,163 (Barger); U.S. Pat. No. 5,191,141 (Barger); U.S. Pat. No. 5,126,308 (Barger); U.S. Pat. No. 4,973,792 (Lewis); and U.S. Pat. No. 4,861,938 (Lewis).

Generally, the heavier olefins having six or more carbon atoms per molecule which are produced in commercial ethylene plants are useful for the production of aromatic hydrocarbons. Portions of the olefin product include olefins with four carbon atoms per molecule. This portion includes both mono-olefins and di-olefins and some paraffins, including butane and iso-butane. Because the portion with four carbon atoms per molecule is generally less valuable and requires significant processing to separate di-olefins from the mono-olefins, processes are sought to improve the utilization of this portion of the ethylene plant product and enhancing the overall yield of ethylene and propylene.

As the economy grows and expands, the demand for light olefins will increase. Because of the limited availability and production of light olefins from current methods, new methods are desired for increasing yields from existing sources of hydrocarbons.

BRIEF SUMMARY OF THE INVENTION

The present invention is a process for catalytic cracking of naphtha to ethylene and propylene. In one embodiment, the process comprises contacting a naphtha feedstock with a catalyst under reaction conditions. The catalyst comprises a molecular sieve having substantially non-intersecting 10 membered ring channels with a dimension in the range from about 0.1 micrometers to about 0.3 micrometers in the channel direction. The 10 membered ring channels form elliptical pores with a pore index from about 22 Å$^2$ to about 30 Å$^2$. The catalyst further comprises a composition with a silicon to aluminum ratio from about 20 to 200.

In another embodiment, the invention is a process for catalytic cracking of naphtha to ethylene and propylene. The process comprises contacting a layered catalyst with a naphtha feedstock. The layered catalyst is a molecular sieve with an inner structure having 8 or 10 membered rings, and an outer structure having 10 membered rings.

In another embodiment, the invention is a zeolite for selectively producing ethylene and propylene. The zeolite is a crystal having substantially non-intersecting channels where the crystal has a dimension between 0.1 micrometers and 0.3 micrometers along the direction of the channels. The channels are elliptically shaped pores with a pore index from about 22 Å$^2$ to about 30 Å$^2$. The zeolite has a silicon to aluminum ratio from between 20 and 200 and is characterized by hydrothermal stability up to about 700° C.

In another embodiment, the zeolite further comprises a material wherein there is a gradient of aluminum in the pores. The aluminum has a decreasing concentration in the direction from the pore mouth to the pore interior.

Other objects, advantages and applications of the present invention will become apparent to those skilled in the art after a detailed description of the invention.

DETAILED DESCRIPTION OF THE INVENTION

Figure 1:
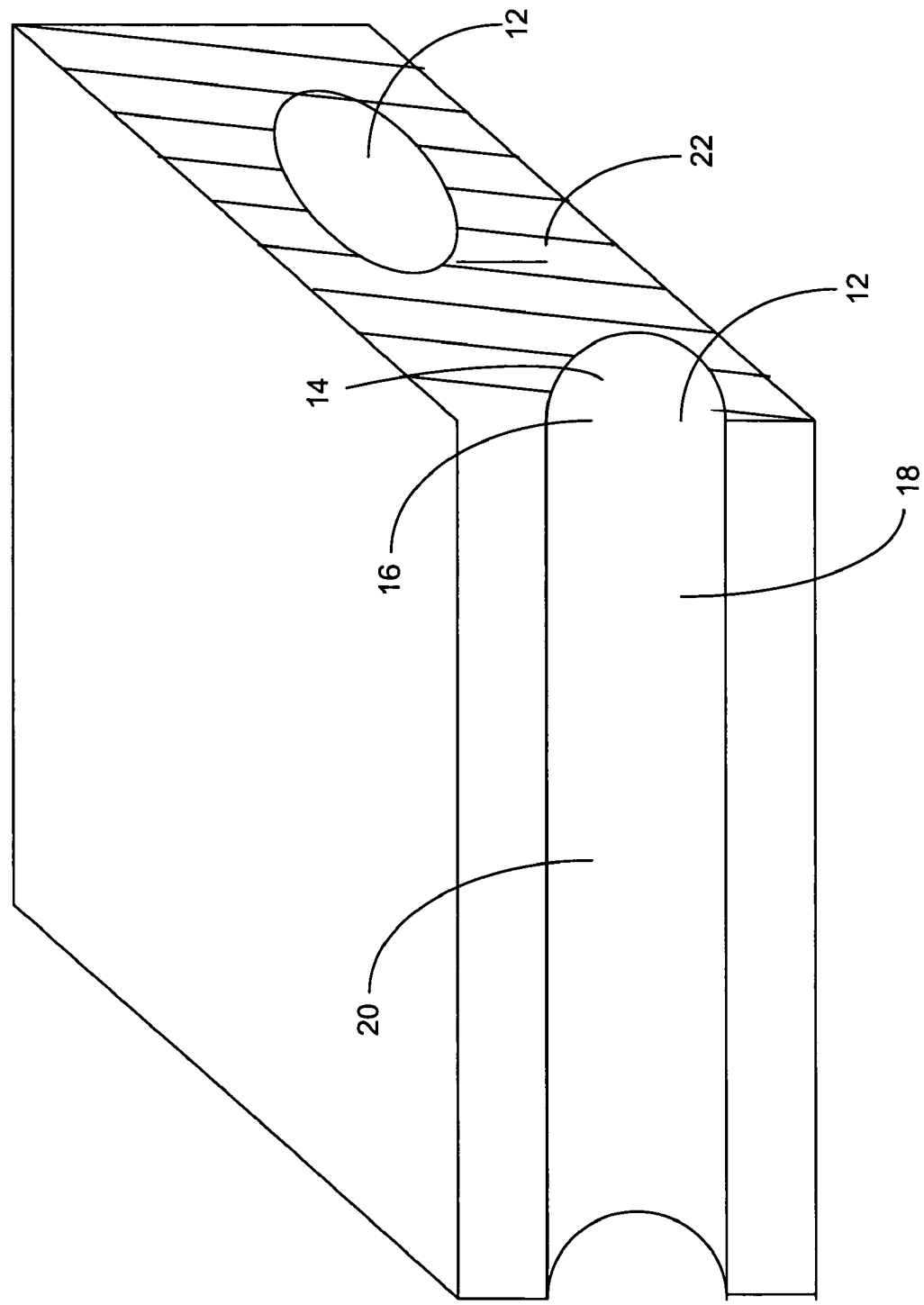
FIG. 1 is a schematic diagram of an idealized pore in a zeolite crystal of the present invention.

One embodiment of the invention is a process for selective catalytic cracking of naphtha to ethylene and propylene. The process comprises contacting a naphtha feedstock with a catalyst and operating the process at reaction conditions.

A necessary feature of the process is the catalyst. The catalyst used is a molecular sieve having pores made of 10 membered rings and having channels with a length between about 0.1 micrometers to about 0.3 micrometers. Additionally, the catalyst has a specifically distributed acid site density in the pores and can be characterized by a silicon to aluminum (Si:Al) atomic ratio from about 20 to about 200. This is equivalent to a silica to alumina ($SiO_2$:$Al_2O_3$) ratio from about 40 to about 400. It is important to prevent reaction of ethylene and propylene to side products, which requires a sufficiently low density of acid sites within the active region of the molecular sieve pores. By using a molecular sieve with a relatively high silica:alumina ratio the acid sites are sufficiently spaced.

Optimal catalytic cracking of naphtha to produce ethylene and propylene requires zeolites having pores of sufficient size to admit molecules from the naphtha feed while not too large to promote the formation of aromatics or hydrogen transfer reactions with large transition states. Without being bound by any theory, it is believed that the pores have a generally elliptical shape and have a pore index from about 22 Å$^2$ to about 30 Å$^2$ allowing access of naphtha molecules into the pores. The pore index as used herein is defined as the product of the two principal diameters of a pore having an elliptically shaped cross-section. The elliptical pores can also be circular wherein the pore index is equal to the square of the diameter of a circular pore.

Examples of zeolites and their pore indexes are listed in Table 1, as found in the Atlas of Zeolite Framework Types published by the International Zeolite Association. The Atlas of Zeolite Framework Types is published on the Internet at (visited Aug. 22, 2002) <http://www.iza-structure.org/databases/> and is from Ch. Baerlocher, W. M. Meier and D. H. Olson, "Atlas of Zeolite Framework Types", 5$^{th}$ ed. Elsevier, Amsterdam, 2001.

TABLE 1

| Zeolite | Structure | Pore Dimensions | Pore Index |
|---|---|---|---|
| ITQ-3 | ITE | 3.8 Å by 4.3 Å | 16.3 Å$^2$ |
| ZK-4 | LTA | 4.1 Å by 4.1 Å | 16.8 Å$^2$ |
| SSZ-23 | STT | 3.7 Å by 5.3 Å | 19.6 Å$^2$ |
| EU-1 | EUO | 4.1 Å by 5.4 Å | 22.1 Å$^2$ |
| MCM-22 | MWW | 4.0 Å by 5.5 Å | 22 Å$^2$ |
| Ferrierite | FER | 4.2 Å by 5.4 Å | 22.7 Å$^2$ |
| ZSM-23 | MTT | 4.5 Å by 5.2 Å | 23.4 Å$^2$ |
| ZSM-22 | TON | 4.6 Å by 5.7 Å | 26.2 Å$^2$ |

A preferred zeolite is a ferrierite. Ferrierite is a two-dimensional channel zeolite structure with 8 and 10 member ring channels. The 10 member channels have an approximately ellipsoid cross section with two diameters defining the ellipsoid of 5.4 Å and 4.2 Å. The ferrierite 10 member rings have substantially non-intersecting channels.

The synthesis of zeolites of the present invention can be formed by hydrothermal crystallization from a reaction mixture containing the desired amounts of silica and alumina and a templating agent. Zeolitic synthesis processes are known in the art, and can be found in U.S. Pat. No. 4,554,143; U.S. Pat. No. 4,440,871; U.S. Pat. No. 4,853,197;

U.S. Pat. No. 4,793,984; U.S. Pat. No. 4,752,651 and U.S. Pat. No. 4,310,440, all of which are incorporated by reference.

An advantage of this process with these zeolites is control over the propylene to ethylene ratio. This process produces a higher ratio of propylene to ethylene and can achieve a ratio of greater than 0.9. Another advantage to the present invention is operation of the process at lower temperatures. The process is operated at about 150° C. to 200° C. lower than conventional steam cracking processes of temperatures around 850° C. This can result in considerable energy savings during operation. There will also be a saving in the cost of equipment of the reactor because of simplification of the metallurgical requirements.

In a second embodiment, the invention is a process for selective catalytic cracking of naphtha to ethylene and propylene. The process comprises contacting a naphtha feedstock with a catalyst and operating the process at reaction conditions. The catalyst uses a molecular sieve made of a layered material comprising at least two layers of zeolite. The layered zeolite includes at least two layers wherein there is at least one inner zeolite layer and at least one outer zeolite layer. The inner zeolite layer has a first structure and includes pores made of 8 membered rings, 10 membered rings, or a mixture of 8 and 10 membered rings. The outer zeolite layer has a second structure and includes pores made of 10 membered rings, wherein the pores of the outer layer overlay the pores of the inner layer.

The inner layer is a zeolite with pores small enough to suppress the formation of aromatics. Examples of such zeolites include, but are not limited to, wenkite, chabazite, dachiardite, erionite, zeolite A, ZK-4, epistilbite, laumontite, wienebeneite, EU-1, UZM-5, UZM-9 and UZM-12. Combinations of zeolites can also be used to form an interior layer, or a plurality of interior layers with one or more of the structures listed. The outer layer is a zeolite with pores large enough to admit the diffusion of naphthenes and isoparaffins that are present in crackable hydrocarbon feedstocks. Examples of such zeolites include, but are not limited to, ferrierite, ZSM-22, ZSM-23, ZSM-50, ZSM-57, ZSM-11, ZSM-5, NU-87 and clinoptilolite. Combinations of zeolites can also be used to form an outer layer, or a plurality of outer layers with one or more of the structures listed.

The resulting layered catalyst is an improved catalyst relative to each of the individual catalysts used for synthesizing the layered catalyst. The improved catalyst will yield higher amounts of ethylene and propylene from a hydrocarbon feedstock because the larger outer pores allow larger hydrocarbon molecules to get in and to get activated. As the molecules diffuse into the smaller pores, the smaller pores restrict the amount of aromatic formation favoring the conversion to light olefins because of the restrictive pore size in the inner layers.

The inner layer, or layers, has a dimension from about 0.1 micrometers to about 5 micrometers, with a preferred dimension of 0.1 micrometers to 0.5 micrometers. This dimension is the thickness of the layers if the layers are grown over an inert core, or the effective diameter of a catalyst particle grown. By effective diameter is meant, for non-spherical shapes, the diameter that the shaped particle would have if it were molded into a sphere. In a preferred embodiment, the dried shaped particles are substantially spherical in shape.

The outer layer, or layers, has a dimension from about 0.1 micrometers to about 1 micrometer, with a preferred dimension from 0.1 micrometers to 0.2 micrometers. The overall dimension of the catalyst particles is preferably in the range of 0.1 micrometers to 5 micrometers with a more preferred range of 0.5 micrometers to 2 micrometers.

In an alternate embodiment, the layered zeolite has an inert inner core. This embodiment comprises an inert inner core and at least one layer of an aluminum containing zeolite on top of the inert core. An inert core as used herein is any material that is unreactive for the present application, and includes cores made of a material that is not accessible to the hydrocarbons with respect to the materials acidity. The inaccessibility can be due to the lack of pores, pores that are to small to admit the hydrocarbons, or a core that has a layer of an inert and impermeable material between the inner core and the zeolite. This allows for the zeolite to be increased in size while maintaining a high surface to volume ratio of the active catalyst region. This embodiment also provides for short active regions accessible to naphtha molecules and limiting the residence times of naphtha molecules in catalytically active regions. This embodiment provides larger crystals that are equivalent to smaller or very thin crystals of zeolite as regards the catalytic performance, such as when the use of larger crystals is necessary and smaller crystals are not practical for hydrocarbon cracking processes. This embodiment, as it can provide a thin reaction zone, can produce higher yields of ethylene and propylene while limiting the amount of ethylene and propylene further reacting to other undesired products. This embodiment also helps to overcome problems associated with limitations associated with intraparticle diffusion.

An optional aspect of the process is using a zeolite with an aluminum concentration decreasing as one moves down a pore from the mouth of the pore to the interior of the pore. FIG. 1 represents a diagram of a pore for an idealized zeolite crystal of the present invention. The zeolite crystal 10 is made up of a series of substantially non-intersecting pores 12. A pore 12 has a pore mouth 16 defined by the edge 14 of the pore 12. The zeolite crystal 10 as used with the present invention has a relatively high aluminum concentration region 18 near the pore mouth 16 with a decreasing aluminum concentration as one moves down the pore 12 away from the pore mouth 16. The crystal 10 has an interior pore region 20 which has a relatively low aluminum concentration. The relatively high and low aluminum concentrations are relative to the overall average aluminum concentration in the zeolite pores 12 framework. A preferred embodiment of the zeolite is for a distribution of aluminum concentration within the pore 12. The preferred distribution is a gradient with a relatively high alumina concentration near the pore mouth and a lower concentration in the pore interior. The preferred gradient is for the relatively high aluminum concentration to be at least 1.5 times as great as the average aluminum concentration in the pores 12.

Another optional aspect of this process is using a zeolite wherein the crystal 10, as shown in FIG. 1, has an exterior surface 22, and the exterior surface 22 has acid sites that are neutralized. This produces an exterior surface 22 that is unreactive when exposed to the naphtha. This presents a zeolite crystal with a sharp increase in aluminum concentration as one traverses from an external surface to just inside a pore, and the aluminum concentration then decreases as one travels down the pore. By neutralizing the acid sites on the external surface, the reaction for cracking a naphtha molecule is prevented on the surface outside of the pores. This prevents the olefinic molecules generated in the pores of the zeolite from further reacting to produce undesirable products. This also limits the production of larger olefins and aromatics that might be produced on external surfaces of the zeolite. The exterior surface 22 may be neutralized in a number of ways. One method of neutralizing the zeolite surface 22 is to coat the surface with a non-reactive material, such as continuing growing the crystal with an aluminum free inert material. It is preferred to have a very thin layer of only a few molecules thickness. An alternate to covering the entire zeolite surface 22 is to use a chemical, such as silane, that will cover the surface aluminum. An alternative method of neutralizing the surface is to remove the aluminum on the surface 22 of the zeolite. Removal of the aluminum can be accomplished by treating the zeolite with an appropriate chemical such as EDTA (ethylenediamine tetraacetic acid) or AFS (ammonium hexafluorosilicate).

The naphtha components react with acid sites within the pores and create light hydrocarbons, specifically ethylene and propylene. The acid sites within the pores are sufficiently spaced and have decreasing concentration when one travels from the pore mouth to the interior of the pore. The spacing and decreasing concentration of acid sites inhibits the continuation of reaction to prevent the formation of undesirable products, such as aromatics or subsequent reacting of the ethylene or propylene produced. The spacing and decreasing concentration as well as the pore size and shape of the pores also prevents the formation of aromatics. By using a zeolite with a relatively small pore size also prevents the formation of aromatics in the pores.

An embodiment of this invention is a zeolite structure with unique aluminum distribution and crystal dimensions. A zeolite comprising a crystal having substantially non-intersecting channels is grown. The channels are made of 10 membered rings and the crystal size is limited to less than 0.5 micrometers in the direction of the 10 membered ring channels. A preferred crystal dimension is in the range from about 0.1 micrometers to about 0.3 micrometers.

Figure 3:
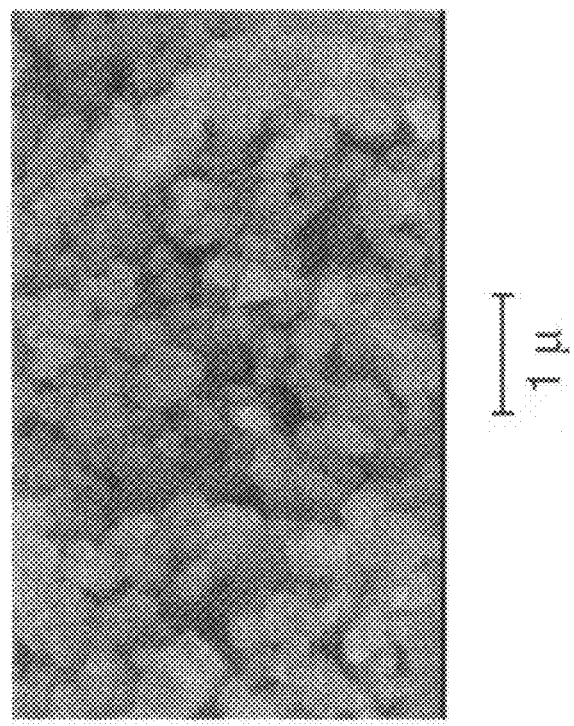
FIG. 3 is a scanning electron micrograph of a ferrierite zeolite formed with a pyrrolidine template.
Figure 2:
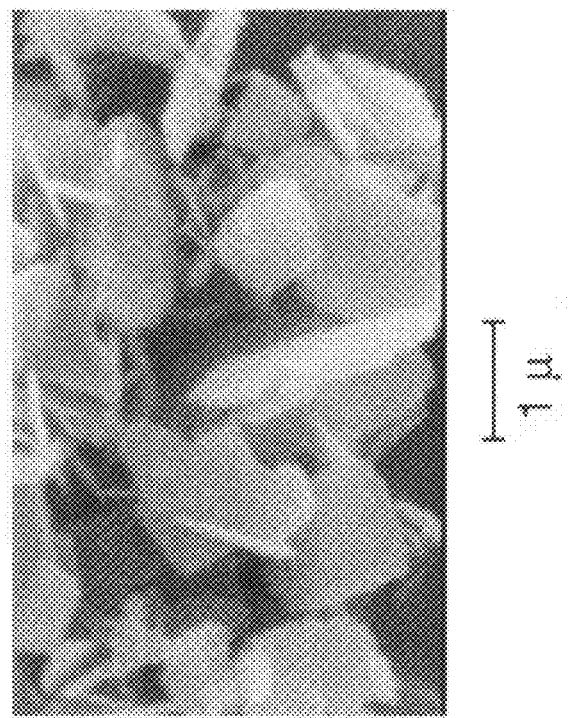
FIG. 2 is a scanning electron micrograph of a ferrierite zeolite formed with a pyridine template.
Figure 4:
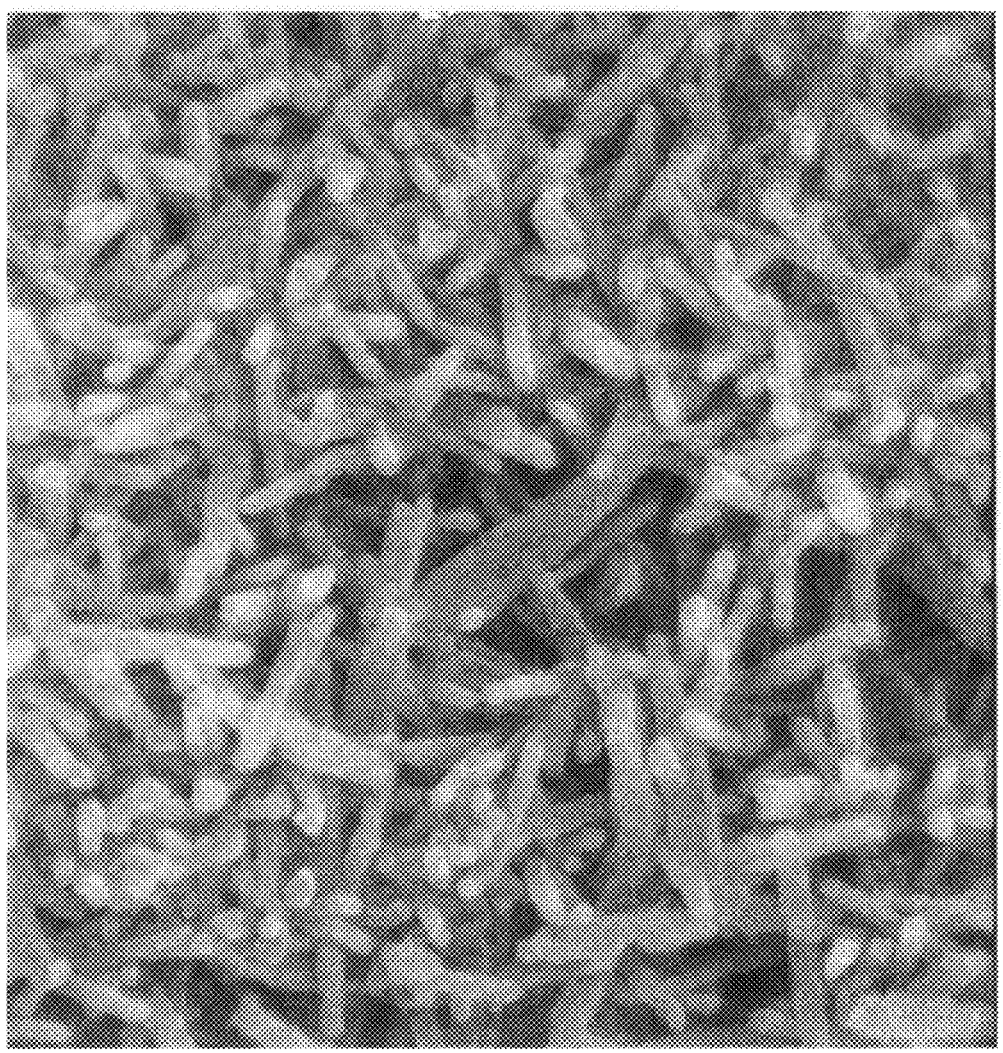
FIG. 4 is a scanning electron micrograph of a conventionally produced ZSM-22 zeolite.
Figure 4:
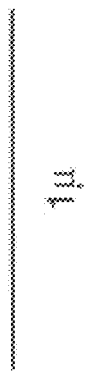
Figure 5:
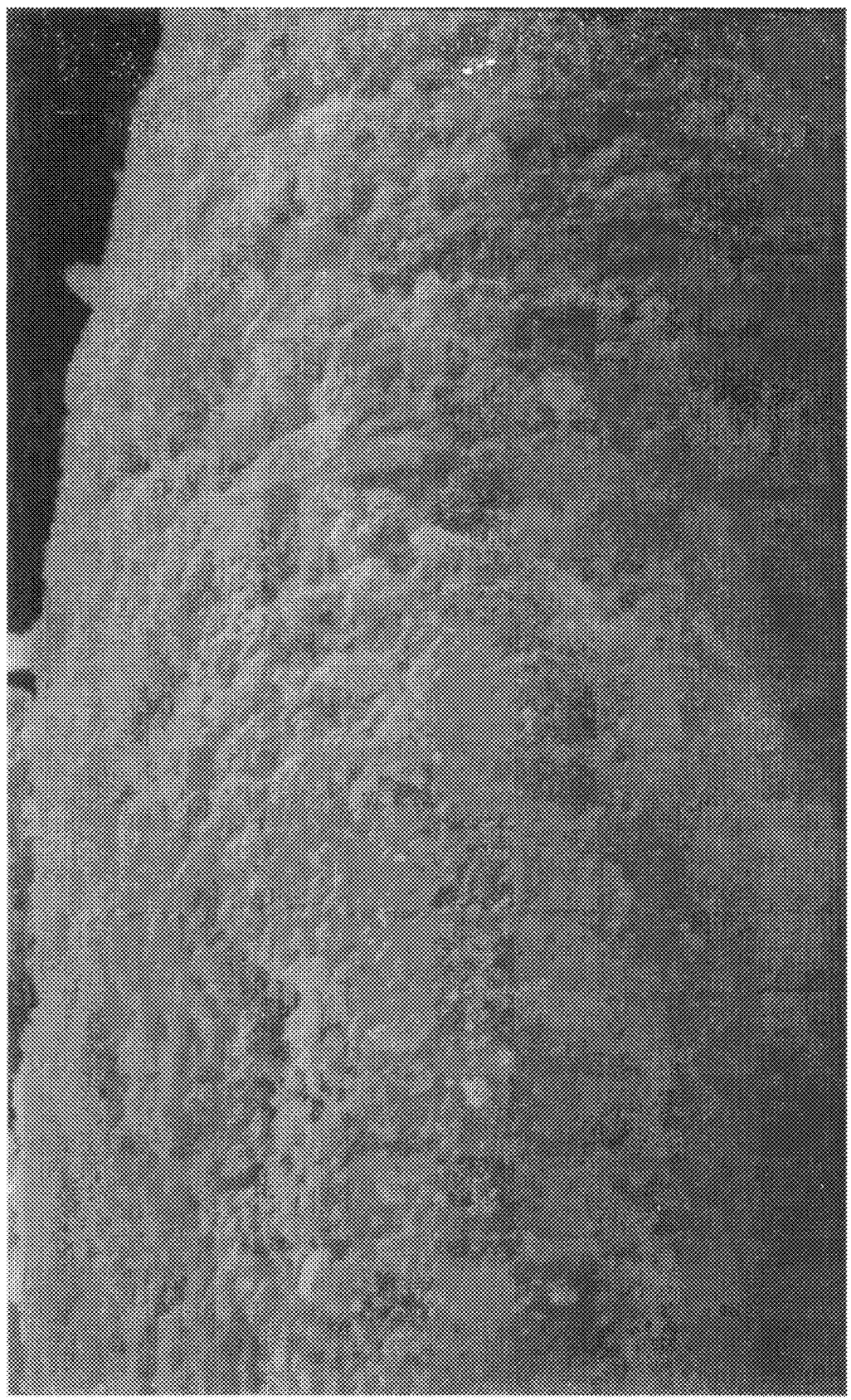
FIG. 5 is a scanning electron micrograph of a microcrystalline produced ZSM-22 zeolite.

An aspect of the invention is the residence time of the hydrocarbon to be reacted in the catalyst pores. Using a catalyst with a relatively short channel length of less than 0.3 micrometers limits the residence time of the hydrocarbon in the pores. The desired morphology of the catalyst is for a relatively short channel length of the pores. The preferred pore channel length is from about 0.1 micrometers to about 0.3 micrometers. The morphology limits the residence time of hydrocarbons within the pore channels. The morphology can be studied with electron microscopy. FIGS. 2 and 3 show scanning electron micrographs (SEM) of ferrierite with two different templates. FIG. 2 shows a pyridine template which produces a conventional platy morphology of the ferrierite. The pyridine templated ferrierite has a silica to alumina ratio of 61.7. FIG. 3 shows a pyrrolidine template of ferrierite producing small crystals. The pyrrolidine templated ferrierite has a silica to alumina ratio of 64.4. From transmission electron microscopy (TEM) the 10 and 8 membered-ring channels of the platy morphology ferrierite are parallel to the plates and consequently are too long. The plates have a thickness of 0.1 to 0.2 micrometers and there are no channels in that direction. Using the pyrrolidine templated ferrierite, smaller crystals are produced with channel lengths in the preferred range. Another zeolite, ZSM-22, is shown in FIGS. 4 and 5. When ZSM-22 is conventionally produced as shown in FIG. 4, a needle like structure is created and the structure has pore channels parallel to the structure's principal axis. The channels are consequently too long. By selection of an alternate template, a microcrystalline ZSM-22 is produced, as shown in FIG. 5. The microcrystalline ZSM-22 has channel lengths in the desired range from about 0.1 to about 0.3 micrometers.

Figure 6:
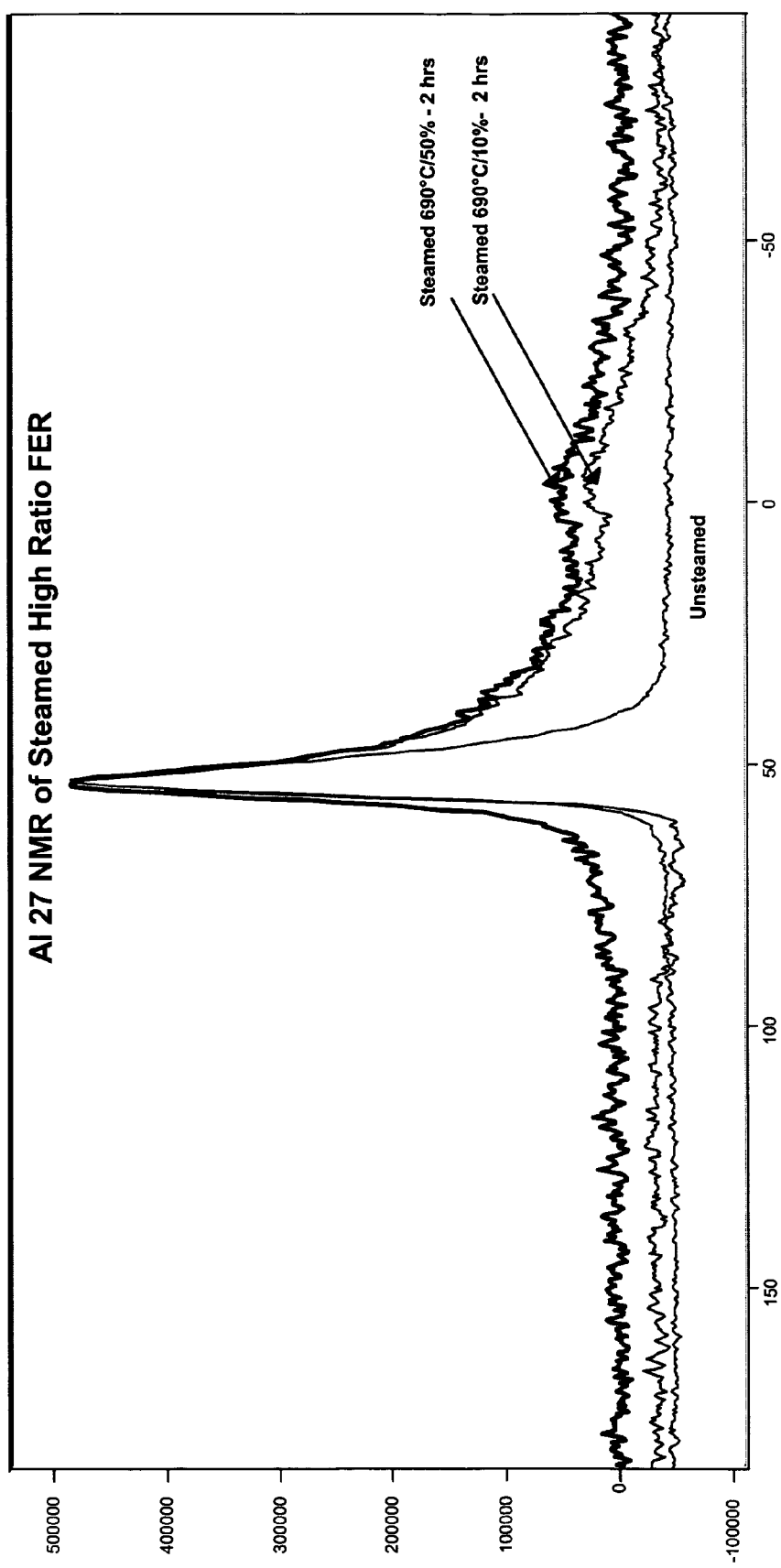
FIG. 6 is an NMR scan of a high ratio ferrierite zeolite before and after subjecting the zeolite to severe steaming procedure.

A preferred zeolite can be found in a modified ferrierite. In ferrierite, the only channels available for bulky reactant molecules in the feed are the 10 membered ring channels. Smaller 8 membered ring channels do not allow access to bulky reactant molecules such as isoalkanes and naphthenes, but do provide access for movement of small product molecules such as ethylene and propylene. The 10 membered ring channels form elliptically shaped pores wherein the elliptical pores have a pore index from about 22 Å$^2$ to about 30 Å$^2$. The zeolite is characterized by a silica:alumina ratio from about 40 to about 400, and further characterized in that the zeolite crystal is hydrothermally stable to about 690° C. The hydrothermal stability is important as the process is carried out at a temperature from about 550° C. to about 700° C., with a preferred range from about 600° C. to about 675° C. The process also includes carrying out catalyst regeneration at a temperature of about 15° C. to 25° C. higher that the inlet reaction temperature. A ferrierite zeolite with the desired properties was tested under severe steaming conditions. Nuclear magnetic resonance (NMR) of the zeolite before and after the severe steaming procedure indicated an effective amount of the framework alumina remained intact, as shown in FIG. 6.

Pore diameter can be controlled by the introduction of non-framework species, for example, by cation exchange. Examples of species for use in cation exchange include, but are not limited to, transition metals, non-framework aluminum, potassium, sodium, magnesium, calcium, strontuim, phosphorus, and mixtures thereof.

An alternate embodiment of a zeolite of the present invention is a layered zeolite. The layered zeolite is characterized by an inner structure having pores small enough to suppress aromatic formation from ethylene and propylene, and an outer layer having larger pores for admitting naphthenes and iso-paraffins. The inner layers have pores made from a zeolitic material having large 8 membered rings or small 10 membered rings. A thin outer layer is then grown epitaxially over the inner layer, where the outer layer has larger 10 membered rings.

Without being bound to a particular theory, it is believed that control of the Al content and its uniform distribution over the potential sites is important to maximizing the activity, selectivity, and stability of molecular sieve for use in the production of light olefins from naphtha.

Preferably, the zeolites include the following additional constraints. During reaction with hydrocarbon feed, channels can be partially or totally blocked as a result of deposition of coke molecules. Blockage can also result from deposition of other molecules such as non-framework aluminum. Partial or complete blockage of a channel will make a portion or all of the channel ineffective for continuing cracking reactions. It is important, therefore, that the channels have a small dimension, while at the same time the catalyst particles must be above a minimum size so as not to be carried out of the reactor with a stream of products.

One method of making these zeolites includes initially growing crystals with an aluminum free material to provide inert inner cores. The inert cores are used as seeds over which an aluminum containing zeolite is grown epitaxially until an outer layer having a desired thickness is achieved. A desired outer layer thickness is in the range from about 0.1 micrometers to about 0.5 micrometers. The outer surface external to the pores is further processed to neutralize the aluminum on the outer surface. One manner of neutralizing this outer surface is to further grow epitaxially a thin layer of aluminum free material.

The process of the invention comprises contacting a naphtha feedstream, in gaseous form, with any of the above described catalysts. The contacting of the naphtha with the catalyst occurs, for example, in a fluidized catalytic cracking (FCC) type reactor. The process entails feeding the hot catalyst and the vaporized, preheated naphtha into a reactor vessel, wherein the catalyst mixes with the gas and is entrained with the gas, and the gas-catalyst mixture reacts under operating conditions producing a product gas and used catalyst. The product gas and used catalyst exit the reactor where the used catalyst is disentrained from the product gas, leaving a product gas stream and a catalyst stream. Some of the catalyst is then sent to a regenerator where carbon deposits are substantially removed. The choice of reactor can be any fluidized type of reactor for intimately mixing the naphtha feedstream with the catalyst. Reactors of this type are well known to those skilled in the art. A fluidized reactor usable in this invention is described in U.S. Pat. No. 6,183,699, which is incorporated by reference.

Alternate feedstocks that are crackable to ethylene and propylene include gas oil, vacuum gas oil, and Fischer-Tropsch wax. Preferably, the feedstock has been processed to remove aromatics. An optional configuration in the present invention includes a hydrocarbon separation unit, for processing the product gas stream. The product gas stream is separated into an ethylene product stream, a propylene product stream, and a plurality of recycle streams. The recycle streams are optionally further separated into an ethane stream, a propane stream, a butane and butene stream, and a non-aromatic naphtha liquids stream. The recycle streams are directed back to the reactor and are optionally, directed into the reactor at a single location, at different locations, or even directed to different reactors arrayed in a parallel configuration.

The aspect of using different reactors in a parallel configuration allows for varying control over the temperatures and pressures for the different individual reactors. The different reactors allows for different temperatures of the individual reactors, different operating pressures, and different residence times. The use of different reactors, optionally, allows for the use of different modified catalysts for use with different feedstocks. In the option of using different catalysts, different catalyst regeneration units are also used for regenerating individual types of catalysts directed to the different reactors.

One aspect of the process operating conditions is the temperature at which the reaction is carried out. The reactions can be carried out between a temperature of about 550° C. to about 700° C. A preferred temperature for operating the process is to be in the range from about 600° C. to about 675° C. with a more preferred operating temperature of about 650° C. to about 670° C.

Another aspect of the process is operating the reaction at an elevated pressure. A preferred operating pressure is in the range from about 101 kPa (0 psig) to about 3550 kPa (500 psig). A more preferred operating pressure is from about 135 kPa (5 psig) to about 450 kPa (50 psig).

Another aspect of the process is the optional further addition of a steam diluent, wherein the steam diluent is injected into the mixture at a rate of up to five times the hydrocarbon ratio on a volume, or mole, basis in the gas phase. The performance can be enhanced by lowering the partial pressure of the hydrocarbons. Adding a diluent, such as steam or an inert gas, lowers the partial pressure while maintaining the operating temperature and pressure of the system.

When the process is carried out in a batch process, the contact time varies from about 0.1 seconds to about 5 hours and preferably from about 0.1 seconds to about 0.1 hour. The longer contact times are used at lower temperatures while shorter times are used at higher temperatures, assuming all other process variables are equal. Further, when the process is carried out in a continuous mode, the weight hourly space velocity (WHSV) based on the total feed (including any diluents) can vary from about 5 $hr^{-1}$ to about 200 $hr^{-1}$ and preferably from about 10 $hr^{-1}$ to about 100 $hr^{-1}$. As is understood in the art, the weight hourly space velocity is the weight flow of the feed divided by the catalyst weight.

Results from runs with the modified zeolites demonstrate the increased conversion. Of note is the increased ratio of propylene to ethylene produced in the conversions. The results of naphtha cracking using several modified zeolites of the present invention are shown in Table 2. The results are for a single pass of naphtha with zeolites in a microactivity test unit. The naphtha is a full boiling naphtha in the $C_5$ to $C_{11}$ range containing about 87% paraffins and naphthenes and about 13% aromatics. The reaction conditions were an inlet temperature of 665° C., reactor pressure of about 150 kPa (7 psig), and a WHSV of about 19 during injection. All of the zeolites were comprised of 80% zeolite and 20% binder. Of note, are the ratios of propylene to ethylene in the tests. The ratio of propylene to ethylene ranged from 0.76 to 1.18. This exhibits the desired ability to increase the propylene yield during the production of ethylene and propylene. In addition, recycling the $C_2$ and heavier hydrocarbons will increase the yield of ethylene and propylene from the naphtha feedstock.

TABLE 2a

|  | Beta 1 | Beta 2 | Omega | Mordenite |
|---|---|---|---|---|
| Pore Size | 6.4 × 7.6 | 6.4 × 7.6 | 7.4 × 7.4 | 6.5 × 7 |
| Pore Size Index | 48.6 | 48.6 | 54.8 | 45.5 |
| $Si/Al_2$ | 24 | 24 | 7 | 20 |
| Ring size | 12 | 12 | 12 | 12 |
| | | Yields, wt. % | | |
| H2 | 3 | 5 | 3 | 3 |
| $C_1$—$C_2$ | 12 | 20 | 13 | 17 |
| $C_2$= | 1 | 2 | 7 | 2 |
| $C_3$= | 0 | 1 | 4 | 1 |
| $C_3$—$C_4$ | 1 | 1 | 19 | 2 |
| $C_5$+ | 46 | 26 | 33 | 41 |
| Coke | 37 | 45 | 21 | 34 |

TABLE 2b

|  | EU-1 | Ferrierite | ZSM-22 | ZSM-23 |
|---|---|---|---|---|
| Pore Size | 4.1 × 5.4 | 4.2 × 5.4 | 4.4 × 5.5 | 4.5 × 5.2 |
| Pore Size Index | 22.1 | 22.7 | 24.2 | 23.4 |
| $Si/Al_2$ | 26 | 76 | 60 | 50 |
| Ring size | 10 | 10 | 10 | 10 |
| | | Yields, wt. % | | |
| H2 | 1 | 1 | 1 | 1 |
| $C_1$—$C_2$ | 9 | 9 | 12 | 12 |
| $C_2$= | 16 | 17 | 17 | 17 |
| $C_3$= | 13 | 18 | 15 | 16 |
| $C_3$—$C_4$ | 14 | 12 | 10 | 11 |
| $C_5$+ | 43 | 40 | 40 | 39 |
| Coke | 4 | 3 | 5 | 4 |

Tables 2a and 2b show the yields of several templated zeolites having the desired properties and several zeolites having undesired properties. The main feature screened shows that zeolites having high pore size indices, or ring sizes larger than 10 membered rings, have a low selectivity for ethylene and propylene, and therefore are unsuitable for this process.

TABLE 3

| | Catalyst Designation | | | | |
|---|---|---|---|---|---|
| | Ferrierite | ZSM-23 | ZSM-22 | SUZ-4 | EU-1 |
| | Gm zeolite/gm naphtha | | | | |
| | 0.148 | 0.152 | 0.152 | 0.152 | 0.152 |
| | Yields, wt % | | | | |
| $H_2$ | 0.6 | 0.9 | 0.9 | 0.7 | 0.6 |
| $C_1$ | 4.8 | 5.6 | 6.2 | 4.0 | 4.2 |
| $C_2=$ | 17.1 | 17.3 | 17.1 | 12.7 | 15.7 |
| $C_2$ | 4.2 | 4.8 | 5.3 | 2.5 | 4.9 |
| $C_3=$ | 17.6 | 16.2 | 15.1 | 15.0 | 13.1 |
| $C_3$ | 3.2 | 3.8 | 3.5 | 3.3 | 5.5 |
| $C_4=$ | 6.4 | 5.4 | 1.4 | 6.5 | 6.4 |
| $C_4$ | 2.5 | 2.0 | 5.2 | 3.5 | 1.6 |
| $C_5+$ Gas | 30.0 | 33.8 | 34.0 | 36.6 | 34.8 |
| Liquid | 10.3 | 6.2 | 6.2 | 10.2 | 9.0 |
| Coke | 3.3 | 4.0 | 5.1 | 5.0 | 4.2 |
| $C_3=/C_2=$ | 1.03 | 0.88 | 0.88 | 1.17 | 0.83 |
| $C_2=+C_3=$, % | 34.7 | 32.3 | 32.2 | 27.4 | 28.8 |

Figure 7:
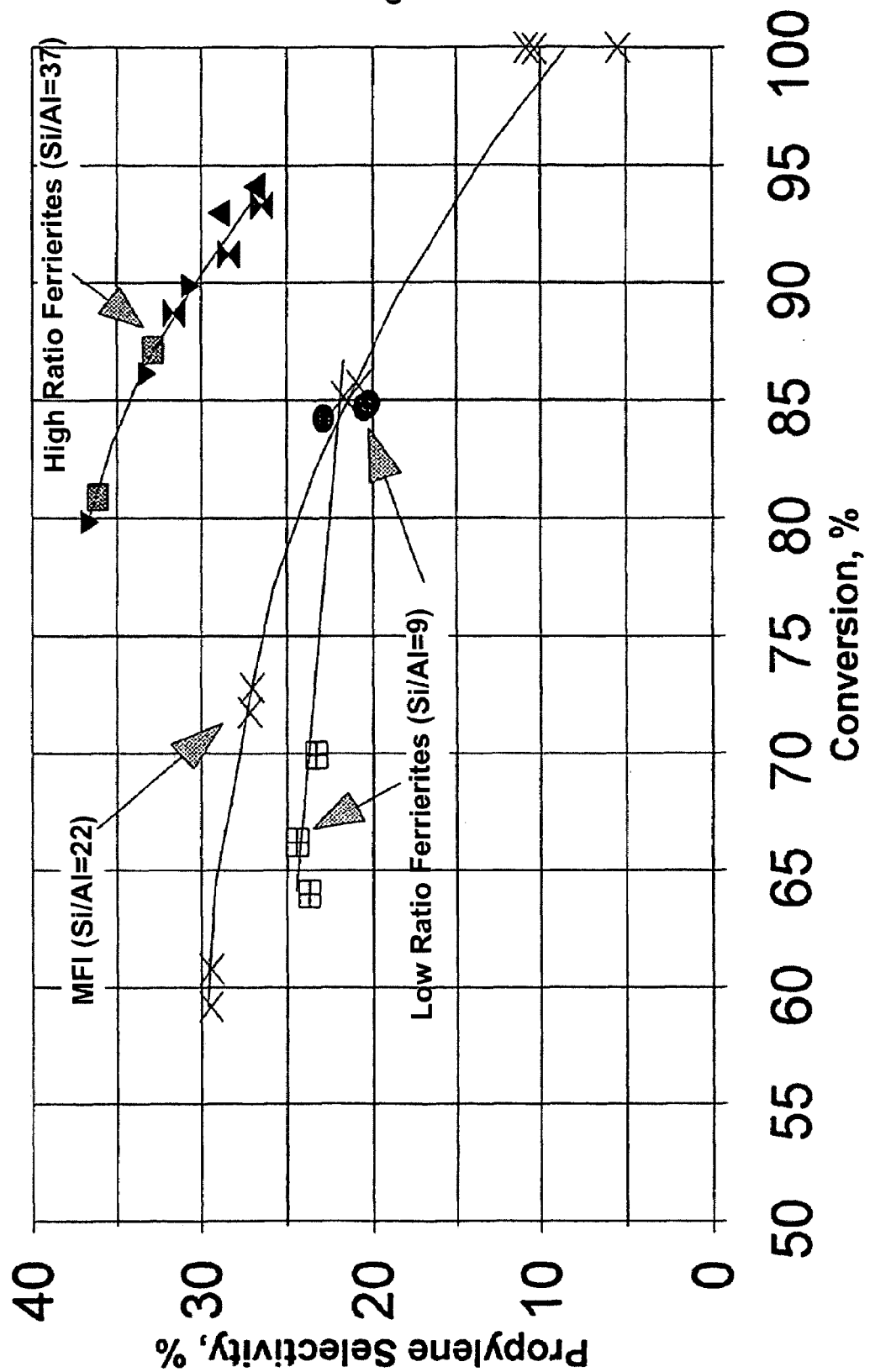
FIG. 7 is a comparison plot for three zeolites of propylene selectivity vs. conversion.
Figure 8:
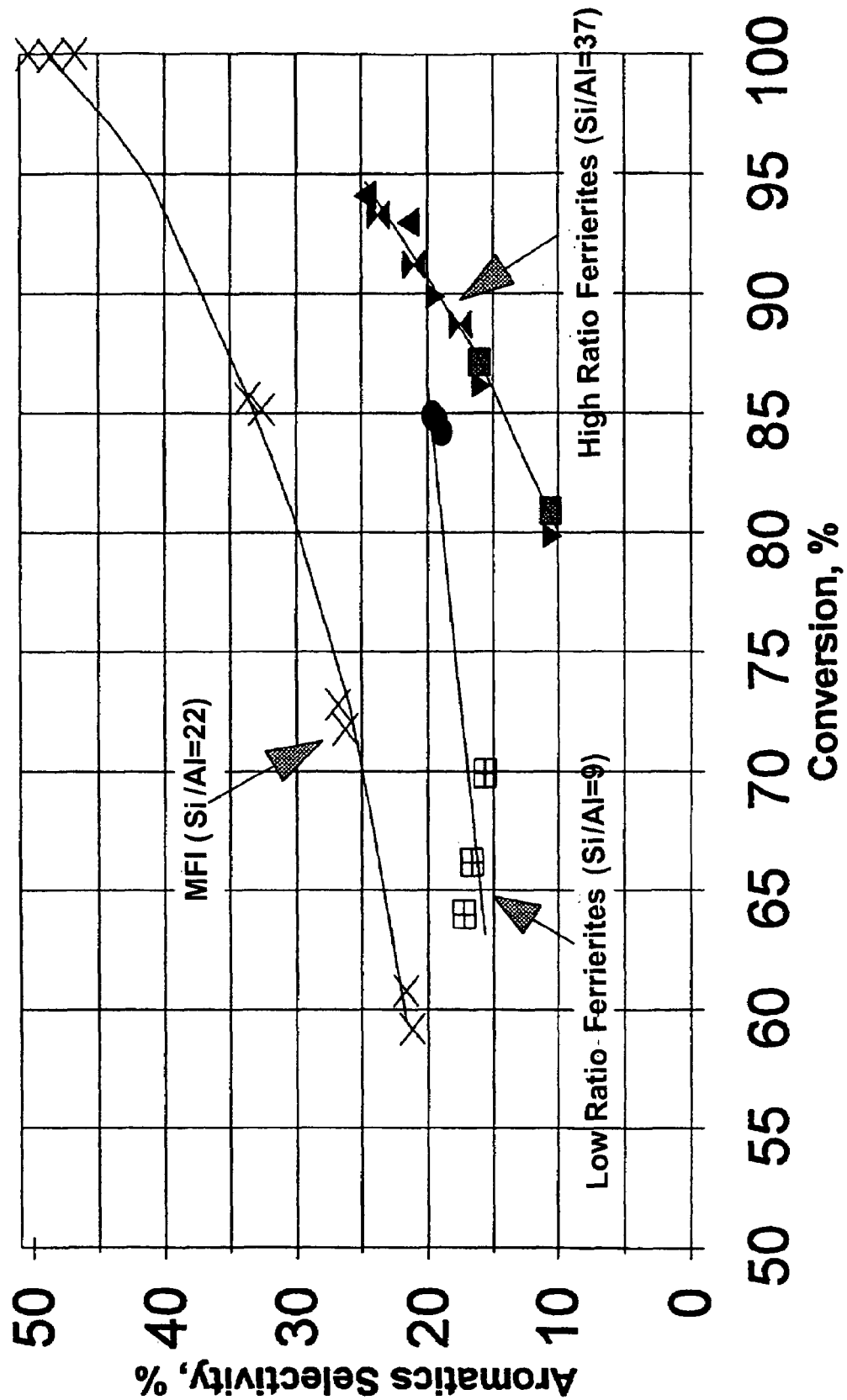
FIG. 8 is a comparison plot for three zeolites of aromatics selectivity vs. conversion.
Figure 9:
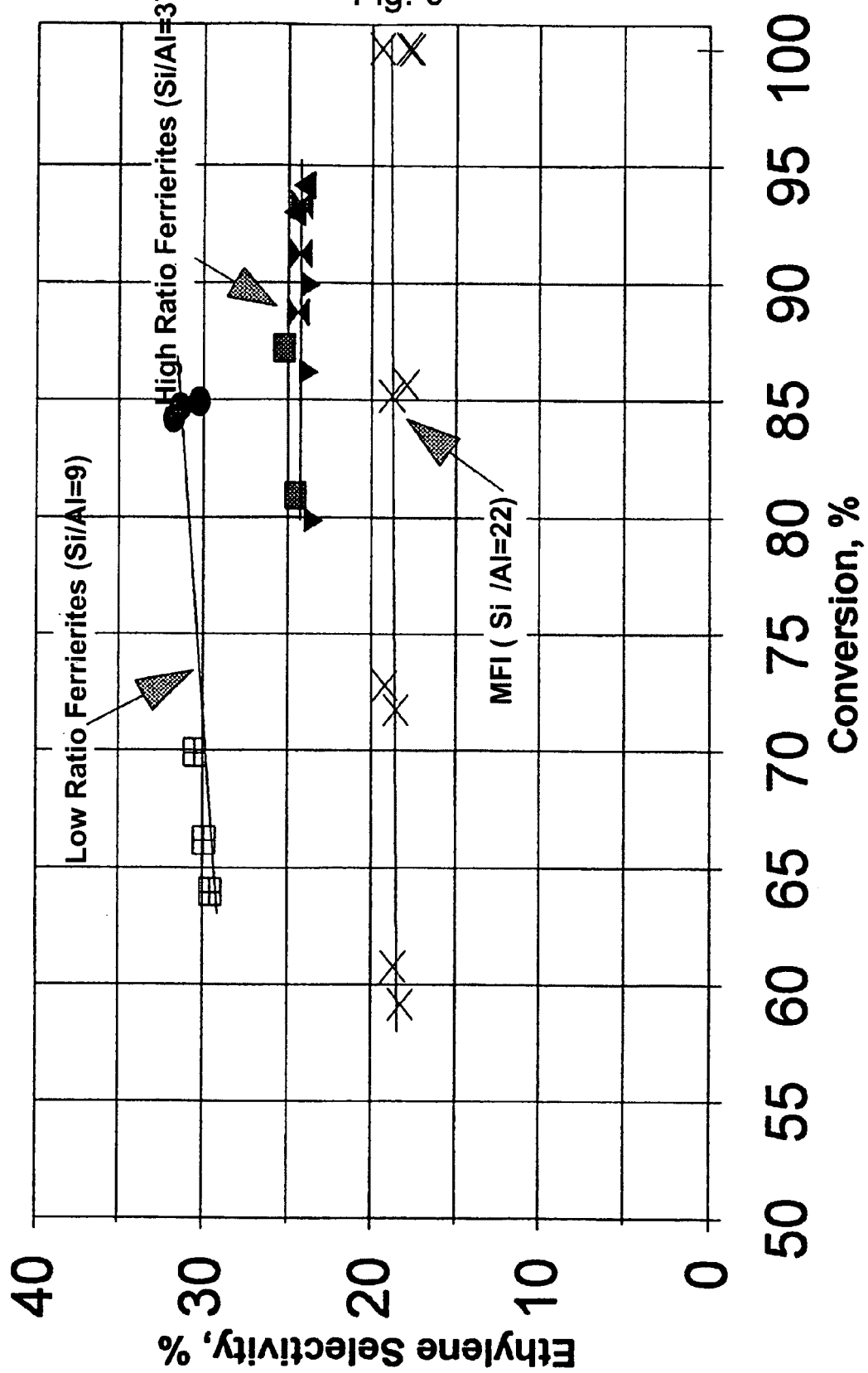
FIG. 9 is a comparison plot for three zeolites of ethylene selectivity vs. conversion.
Figure 10:
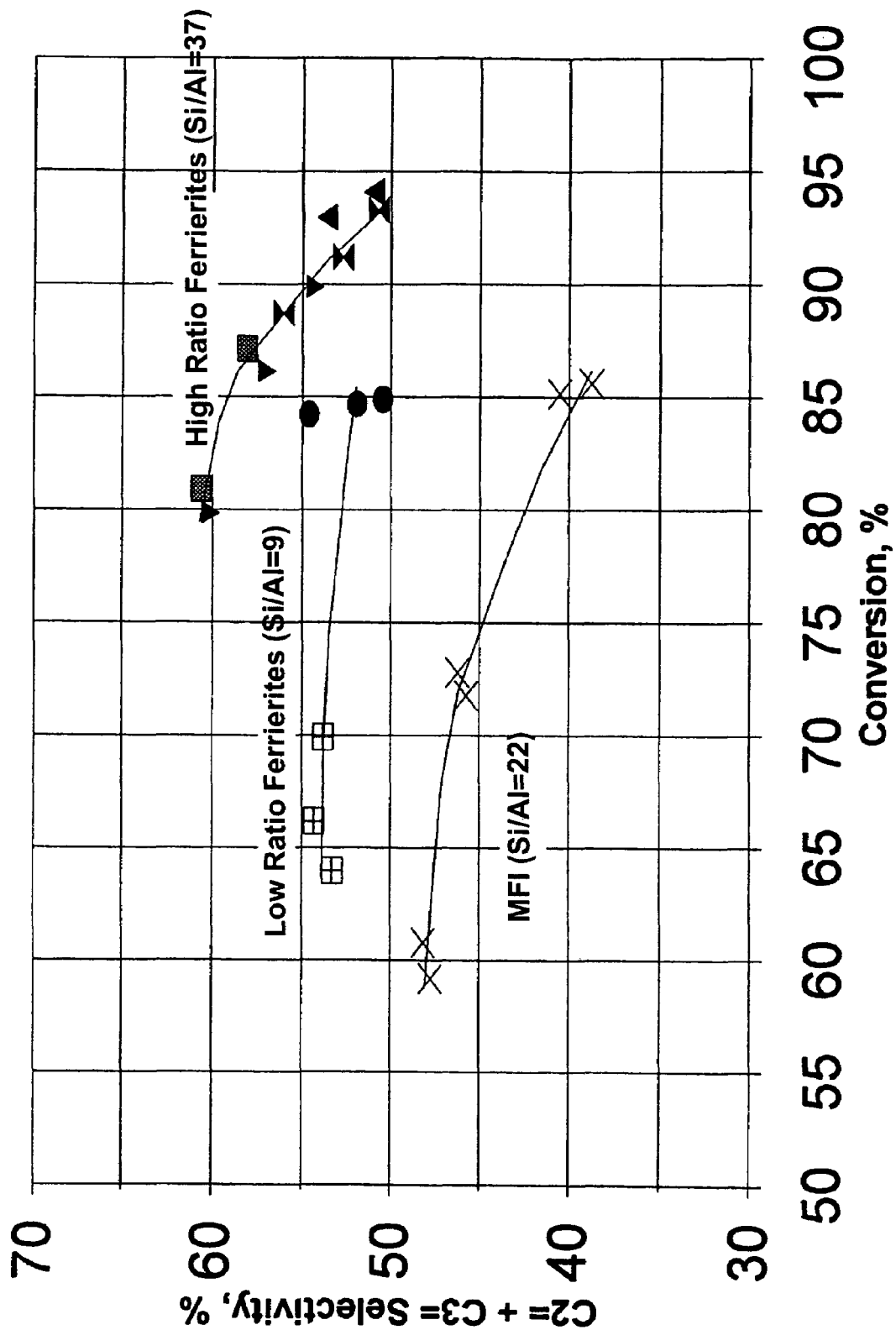
FIG. 10 is a plot showing the increased selectivity and conversion of ethylene and propylene.

Table 3 shows molecular sieves when prepared to produce the desired properties relative to pore size, pore channel length, and acid site density provides good selectivity and conversion of naphtha to propylene and ethylene. This is further illustrated in FIGS. 7 to 10, comparing ferrierite with a zeolite lacking the desired characteristics, i.e. an MFI type zeolite. FIGS. 7 to 10 are for the results of pulse microreactor tests of naphtha cracking over high and low ratio ferrierites and MFI zeolites, showing percent selectivity vs. percent conversion. The high and low ratio refer to the Si:Al atomic ratios. The reaction conditions of the micro-reactor tests are 5000 GHSV (gas hourly space velocity) and a temperature of 650° C. In FIG. 7, the ferrierite, having desired characteristics and prepared with a template, produces a high propylene selectivity and high conversion. FIG. 8 shows the desired ferrierite has a low aromatics selectivity and high conversion when compared with a zeolite having an MFI framework structure and a ferrierite not having desired characteristics (low ratio ferrierite). FIG. 9 shows a comparison of the desired ferrierite with a low ratio ferrierite and a zeolite with, an MFI framework structure for ethylene production. The ethylene selectivity for the ferrierites is greater than the MFI zeolite for which the pore size index is much higher. The templated ferrierite also has an improved conversion over the low ratio ferrierite. The overall improvement is best seen when comparing the total ethylene and propylene selectivity as shown in FIG. 10. The high ratio ferrierite demonstrates significant improvement in selectivity and conversion over a low ratio ferrierite and an MFI zeolite. The MFI zeolite has a 3-d interconnected pore structure and allows for greater conversion of naphtha to aromatics, an undesired product that needs to be separated from any product stream as well as any recycle stream. The disadvantage of the low ratio ferrierite is the high acid site density which causes Al to come out of the framework under simple reaction conditions. The templated ferrierite was made with a lower acid site density than the low ratio ferrierite. By increasing the silica to alumina ratio there is an improvement in propylene selectivity and naphtha conversion, while maintaining a low aromatics generation.

TABLE 4

| Cat. Designation | Low ratio Fer | High ratio Fer | ZSM-35 Fer |
|---|---|---|---|
| $Si/Al_2$ | 17 | 74 | 20.1 |
| Crystallite size, micrometers | 1-2 | 1-2 | 0.2 |
| Conversion | 52 | 79 | 82 |
| | Selectivities | | |
| $H_2$ | 1 | 1 | 2 |
| $C_1$ | 10 | 7 | 14 |
| $C_2=$ | 26 | 25 | 25 |
| $C_2$ | 7 | 6 | 10 |
| $C_3=$ | 28 | 26 | 21 |
| $C_3$ | 3 | 5 | 3 |
| $C_4=$ | 10 | 9 | 7 |
| $C_4$ | 3 | 4 | 4 |
| Aromatics | 4 | 13 | 1 |
| Coke | 8 | 4 | 13 |

Table 4 further lists a comparison of two aspects of the invention showing a comparison of the results of tests using a low ratio ferrierite, a high ratio ferrierite and a ferrierite with a small crystalline size. The tests were run in a microreactor with an inlet feed temperature of 665° C., other operating conditions were as described above. A comparison of the low ratio ferrierite with the high ratio ferrierite shows significant improvement in the conversion of the naphtha feed. In addition, a comparison of the low ratio ferrierite with relatively large crystallite size of 1-2 micrometers, with a low ratio ferrierite having a small crystallite size of 0.2 micrometers demonstrates significant improvement in the conversion of the naphtha feed with decrease in crystal size. These are further demonstrations of the importance of the silicon to aluminum atomic ratio and the control of the size of channels within the crystal through the sizing of the catalyst crystals.

Without being bound by any theory, it is believed that the improvement in ethylene and propylene production results from the combined characteristics of the molecular sieves defined in this invention. The pore must be of sufficient size to permit entry by larger hydrocarbons, particularly isoparaffins and naphthenes. At the same time the pores must be sufficiently small to inhibit the production of aromatic compounds within the pores but not limit the cracking to lower molecular weight olefins. The acid sites need sufficient spacing, or low enough alumina density, to limit undesirable reactions of ethylene and propylene, and to minimize the removal of Al from the framework under calcination, reaction and regeneration conditions. The residence time within the pores is an additional factor controlling the production of ethylene and propylene, and one which is controlled by limiting the length of the pore channels.

While the invention has been described with what are presently considered the preferred embodiments, it is to be understood that the invention is not limited to the disclosed embodiments, but is intended to cover various modifications and equivalent arrangements included with the scope of the appended claims.

The invention claimed is:

1. A process for selective catalytic naphtha cracking to ethylene and propylene comprising contacting a naphtha feedstock with a catalyst at reaction conditions to produce ethylene and propylene, the catalyst comprising a layered molecular sieve comprising an inner core having pores made of 8 or 10 membered rings having a first three dimensional framework structure, and an outer layer having pores made of 10 membered rings having a second three dimensional framework structure, said inner core comprises a zeolite selected from the group consisting of wenkite, chabazite, dachiardite, erionite, zeolite A, ZK-4, epistilbite, laumontite, wienebeneite, EU-1, UZM-5, UZM-9, UZM-12 and mixtures thereof and said outer layer comprises at least one layer comprising a zeolite selected from the group consisting of ferrierite, ZSM-22, ZSM-23, ZSM-50, ZSM-57, ZSM-11, ZSM-5, NU-87, clinoptilolite, and mixtures thereof wherein the pores in the second structure overlay the pores in the first structure.

2. The process of claim 1 wherein the reaction conditions include operating at a temperature in the range from about 550° C. to about 700° C.

3. The process of claim 1 wherein the reaction conditions include a pressure in the range from about 135 kPa (5 psig) to about 450 kPa (50 psig).

4. The process of claim 1 further comprising adding a steam diluent, wherein the steam diluent is fed in a volume ratio to the naphtha feedstock in the range from greater than 0 to about 5.

5. The process of claim 1 wherein the external surface has acidic sites which have been substantially neutralized.

* * * * *